United States Patent [19]

Kolar et al.

[11] Patent Number: 4,730,069
[45] Date of Patent: Mar. 8, 1988

[54] CIS-PLATINUM COMPLEXES WITH A PENTAERYTHRITOL DERIVATIVE AS THE LIGAND, A PROCESS FOR THEIR PREPARATION AND A PHARMACEUTICAL AGENT CONTAINING THESE COMPOUNDS

[75] Inventors: Cenek Kolar; Hans P. Kraemer, both of Marburg; Konrad Dehmel, Marburg-Michelbach, all of Fed. Rep. of Germany

[73] Assignee: Behringwerke Aktiengesellschaft, Fed. Rep. of Germany

[21] Appl. No.: 770,996

[22] Filed: Aug. 30, 1985

[30] Foreign Application Priority Data

Sep. 3, 1984 [DE] Fed. Rep. of Germany ....... 3432320

[51] Int. Cl.$^4$ .............................................. C07F 15/00
[52] U.S. Cl. ..................................... 556/137; 536/51; 536/112; 549/356; 549/377
[58] Field of Search ................... 556/137; 536/51, 112; 549/356, 377

[56] References Cited

U.S. PATENT DOCUMENTS

| | | | |
|---|---|---|---|
| 4,250,189 | 2/1981 | Hydes et al. | 556/137 |
| 4,410,544 | 10/1983 | Berg et al. | 556/137 |

FOREIGN PATENT DOCUMENTS

| | | | |
|---|---|---|---|
| 2024823 | 1/1980 | United Kingdom | 556/137 |
| 2128615 | 5/1984 | United Kingdom | 556/137 |

*Primary Examiner*—Helen M. S. Sneed
*Attorney, Agent, or Firm*—Finnegan, Henderson, Farabow, Garrett and Dunner

[57] ABSTRACT

Compounds of the general formulae I and II

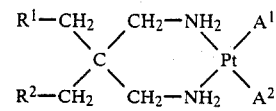

Formula I

-continued

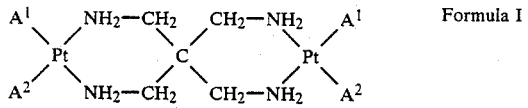

Formula II in which $R^1$ and $R^2$ independently of one another represent $H-(CH_2)_a-(O-(CH_2)_b)_c-O$, where $a=0$ to 4, $b=1$ to 4 and $c=1$ to 7, an alkoxy or arylalkoxy group with 1 to 20 carbon atoms, an alkane- or aralkanesulfonyloxy group with 1 to 7 carbon atoms or a tetrahydropyranyloxy radical, or $R^1$ and $R^2$ together represent an oxygen atom bonded in an ether-like manner or an acetal or ketal radical

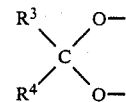

where $R^3$ and $R^4$ independently of one another represent a hydrogen atom, an alkyl group with 1 to 20 carbon atoms of a phenyl group, $A^1$ and $A^2$ are identical and represent a hydroxyl group, chloride, bromide, iodide, nitrate, acetate, trifluoroacetate, trifluorosulfonate or perchlorate, or $A^1$ represents sulfate or carbonate ion and $A^2$ represents $H_2O$, or $A^1 A^2$ together represent the dianion of an organic acid, such as oxalic, malonic, hydroxymalonic, ethylmalonic, succinic, maleic, aconitic, 3,6,9-trioxaundecanedioic, 1,1- or 1,2-cyclobutanedicarboxylic, phthalic, 3- or 4-carboxyphthalic or 3,4-dicarboxyphthalic acid, or $A^1$ and $A^2$ together represent a recurring anionic unit of a polymeric compound, such as dextran sulfate, chondroitin sulfate or galactan sulfate, polyglutamic acid or polyitaconic acid, and a process for their preparation and a medicament containing these compounds are described.

1 Claim, No Drawings

CIS-PLATINUM COMPLEXES WITH A PENTAERYTHRITOL DERIVATIVE AS THE LIGAND, A PROCESS FOR THEIR PREPARATION AND A PHARMACEUTICAL AGENT CONTAINING THESE COMPOUNDS

The invention relates to novel platinum compounds, a process for their preparation and a pharmaceutical agent containing these novel compounds. The compounds are platinum(II)-diamine complexes of the formulae I and II

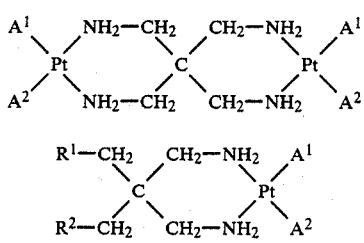

in which

R$^1$ and R$^2$ independently of one another represent H—(CH$_2$)$_a$—(O—(CH$_2$)$_b$) $_c$—O, where a=0 to 4, b=1 to 4 and c=1 to 7, an alkoxy or arylalkoxy group with 1 to 20 carbon atoms, an alkane- or aralkanesulfonyloxy group with 1 to 7 carbon atoms or a tetrahydropyranyloxy radical, or R$^1$ and R$^2$ together represent an oxygen atom bonded in an ether-like manner or an acetal or ketal radical

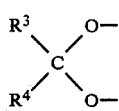

where R$^3$ and R$^4$ independently of one another represent a hydrogen atom, an alkyl group with 1 to 20 carbon atoms or a phenyl group, A$^1$ and A$^2$ are identical and represent the hydroxyl group, chloride, bromide, iodide, nitrate, acetate, trifluoroacetate, trifluorosulfonate or perchlorate, or A$^1$ represents sulfate or carbonate and A$^2$ represents H$_2$O, or A$^1$ and A$^2$ together represent the dianion of an organic acid, such as oxalic, malonic, hydroxymalonic, ethylmalonic, succinic, maleic, aconitic, 3,6,9-trioxaundecanedioic, 1,1- or 1,2-cyclobutanedicarboxylic, phthalic, 3- or 4-carboxyphthalic or 3,4-dicarboxyphthalic acid, or A$^1$ and A$^2$ together represent a recurring anionic unit of a polymeric compound, such as dextran sulfate, chondroitin sulfate or galactan sulfate, polyglutamic acid or polyitaconic acid.

It is known that cis-platinum complexes of the general formula cis-L$_2$PtX$_2$, in which L is a neutral ligand, such as NH$_3$ or an organic amine, and X is an anionic ligand, such as chloride or an anion of an organic acid, have an antitumoral action (Cisplatin-Current Status and New Developments; editors A. W. Prestayko, S. T. Crooke and S. K. Carter, Academic Press, 1980). Cis-platinum(II)-diamine dichloride has been introduced as a medicament.

Cis-platinum complexes which possess alkyl-, aryl- or aralkyl-propyl-1,3-diamine derivatives as ligands are described in German Patent No. 3,337,333-A1 and Dutch Offenlegungsschrift No. 7,904,740.

European Patent No. A-0,098,135 also describes propyl-1,3-diamino ligands which carry alkyl or hydroxyalkyl substituents.

The renal and bone-marrow toxicity of the alkyldiamine-platinum complexes and their low solubility are disadvantages.

The object of the present invention was to prepare novel cis-platinum complexes in which the pentaerythritol structure functions as a bidentate diamino ligand and a therapeutically acceptable anionic compound is present as a ligand, and which have a lower renal and bone-marrow toxicity than the cis-platinum(II)-diamine dichloride which has been introduced into clinical practice.

This object was achieved by preparing compounds with the above formulae I and II and with the definitions given for these formulae, and by testing these compounds for cytostatic activity.

It has been found, surprisingly, that the pentaerythritol derivative cis-platinum complexes of the general formulae I and II have a cytostatic action and considerably more favorable biological properties, such as low renal and bone-marrow toxicity, and physical properties, such as better solubility in an aqueous medium, than the parent compound cis-(NH$_3$)$_2$PtCl$_2$.

Compounds which are preferred in the context of the invention are those of the general formulae I, III, IV and V

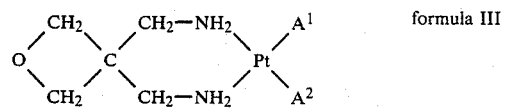

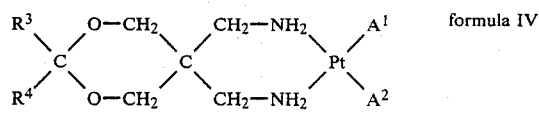

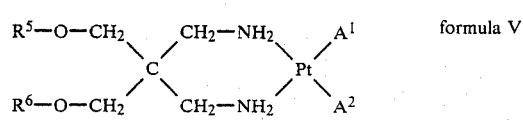

in which

R$^3$ and R$^4$ independently of one another represent H, —(CH$_2$)$_n$—CH$_3$, where n=0, 9 or 17, or phenyl, R$^5$ and R$^6$ independently of one another represent CH$_3$—(OCH$_2$CH$_2$)$_c$— where C=3 or 6, —(CH$_2$)$_n$CH$_3$, where n=0, 9 or 17, or a tetrahydropyranyl, methanesulfonyl or para-toluenesulfonyl group, A$^1$ and A$^2$ are identical and represent chloride, iodide, nitrate, hydroxyl, acetate, trifluoroacetate, trifluorosulfonate, p-toluenesulfonate or perchlorate, or A$^1$ represents sulfate or carbonate and A$^2$ represents H$_2$O, or A$^1$ and A$^2$ together represent the dianion of malonic, maleic, 1,1- or 1,2-cyclobutanedicarboxylic, 3- or 4-carboxyphthalic or 3,6,9-trioxaundecanedioic acid, or A$^1$ and A$^2$ together represent a recurring anionic unit of polyglutamic acid or chondroitin sulfate.

The process according to the invention for the preparation of the compounds of the formulae I and II comprises (a) converting pentaerythritol, in a manner which is known per se, into neopentyltetramine or a neopentyldiazide compound of the general formula VI

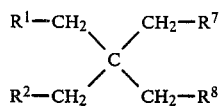    formula VI in which $R^1$ and $R^2$ independently of one another represent OH, $H-(CH_2)_a-(O-(CH_2)_b)_c-O$, where $a=0$ to 4, $b=1$ to 4 and $c=1$ to 7, an alkoxy or aralkoxy group with 1 to 20 carbon atoms or alkane- or aralkane-sulfonyloxy group with 1 to 7 carbon atoms or a tetrahydropyranyloxy radical, or
$R^1$ and $R^2$ together represent an oxygen atom bonded in an ether-like manner or a radical

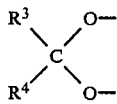

where $R^3$ and $R^4$ independently of one another represent a hydrogen atom, an alkyl group with 1 to 20 carbon atoms or a phenyl group and $R^7$ and $R^8$ are azido groups, and hydrogenating the resulting diazido compound in the presence of palladium-on-charcoal and an organic solvent, such as methanol, ethyl acetate or dioxane, or reducing it with a reducing agent, such as sodium borohydride, a diamino compound of the formula VI, in which $R^1$, $R^2$, $R^3$ and $R^4$ are unchanged and $R^7$ and $R^8$ are amino groups, being formed;

(b) reacting the product from stage (a) in a manner which is known per se with $K_2PtX_4$, in which X represents a chloride or iodide ion, in the presence of a solvent, such as water, dimethylformamide or dimethyl sulfoxide or mixtures thereof with tetrahydrofuran, dioxane, methanol or ethylene glycol dimethyl ether, at a temperature of 0° C. to 80° C. preferably 10° C. to 40° C., to give reaction products of the general formulae I, III, IV and V, in which the radicals R3, R4, R5 and R6 have the meaning already given and $A^1$ and $A^2$ are chloride or iodide;

(c) reacting the product from stage (b) in a manner which is known per se with an inorganic or organic silver(I) compound, such as silver oxide, nitrate, sulfate, carbonate, perchlorate, acetate, trifluoroacetate, trifluorosulfonate or para-toluenesulfonate, in the presence of water or an organic solvent, such as dimethylformamide, dimethyl sulfoxide, tetrahydrofuran, dioxane or methanol or aqueous mixtures thereof, to give compounds of the general formulae I, III, IV and V, in which $A^1$ and $A^2$ represent hydroxyl groups or an anion of the silver compound employed;

(d) replacing the anionic ligands $A^1$ and $A^2$, preferably nitrate or perchlorate, in the product from stage (b) in a manner which is known per se by an anionic compound which is derived from an alkali metal salt of a carboxylic or oligocarboxylic acid. Such anionic compounds are dicarboxylic acids, such as oxalic, malonic, hydroxymalonic, succinic, maleic or 1,1- or 1,2-cyclobutanedicarboxylic acid, phthalic acids, 3,6,9-trioxaundecanedioic acid, tri- or oligo-carboxylic acids, such as aconitic acid, 3- or 4-carboxyphthalic acid, 3,4-dicarboxyphthalic acid or polymeric compounds, such as polyglutamic acid, polyitaconic acid, dextran sulfate, chondroitin sulfate or galactan sulfate.

The invention also relates to medicaments containing one or more of the compounds of the formulae I and II as active compounds.

Besides the customary pharmaceutical formulating agents and/or diluents, these medicaments can optionally also contain, in addition to the compounds of the general formulae I and II, other active compounds to assist in the therapy as long as these do not display any undesirable side-effects together with the compounds of the formulae I and II according to the invention. The dosage and method of use essentially correspond to those for cis-$(NH_3)_2PtCL_2$, but higher dosages and/or more frequent administration are also possible, because of the wider therapeutic range (lower toxicity) of the compounds according to the invention.

Determination of the cytostatic activity

The cytostatic activity of the compounds described here was determined on L1210 leukemia cells from mice. In detail, the following test systems were used:

(a) Proliferation assay

In this method, the extent to which cells incorporate radioactively labeled DNA precursors (for example C14-labeled thymidine) in vitro, after incubation of the cells with different concentrations of the test substance, is determined. Untreated L1210 cells are subjected to the same test conditions and serve as a control. The method is briefly described below:

L1210 cells in the exponential growth phase ($5 \times 10^3$/ml in RPMI 1640) are incubated with different concentrations of the test substance in a microtitration plate for 72 hours (37° C., 5% by volume of $CO_2$, 95% relative atmospheric humidity). Controls comprise cells which are incubated only with fresh medium. All the determinations are carried out as quadruplicate determinations. After 65 hours, 50 μl of C14-thymidine (1.5 uCi/ml) are added in order to radioactively label the DNA of the cells. After incubation for 7 hours, the cells are filtered off with suction, the DNA is precipitated with 5% strength trichloroacetic acid and the precipitate is washed successively with water or methanol.

After drying at 50° C., the radioactivity incorporated in the DNA is determined, after addition of 5 ml of scintillation liquid.

The results are expressed as the scintillation index after incubation with the test substance as a percentage of the untreated control. From the measurement values thus obtained, the dose/effect curve is plotted and the $IC_{50}$, i.e. the concentration which reduces the incorporation of radioactive thymidine by 50% in comparison with the control under the test conditions, is determined graphically. The IC50 values of the compounds described here have been summarized in comparison with cisplatin (DDP) in Table 1.

(b) Colony formation of L1210 leukemia cells in soft agar

This method serves to demonstrate an influence of the test substances on the growth behavior of the cells over several generations (with a cell cycle time of 10–12 hours, about 14 successive generations are observed in the test period of 7 days). In this test, substances which have a cytostatic action cause a reduction in the colony count to be observed in comparison with an untreated control. In detail, the test is carried out as follows:

500 leukemia cells per plate are incubated with different concentrations of test substance at 37° C. for 1 hour. The cells are then washed twice with McCoy5A medium and finally poured into Petri dishes, after adding 0.3% of agar. Controls are incubated only with fresh medium. Instead of incubation for 1 hour, in some cases different concentrations of test substance are admixed to the upper layer of agar in order thus to achieve continuous exposure of the cells over the entire incubation period. After the agar has solidified, the plates are incubated in an incubating cabinet at 37° C. for 7 days (5% by volume of $CO_2$, 95% relative atmospheric humidity). The number of colonies formed with a diameter of more than 60μ is then counted. The results are expressed as the colony count in treated agar plates as a percentage of that in the untreated control. From the dose/effect curve thus obtained, the $IC_{50}$ is determined as a measure of the efficacy of the substance. The results for the compounds described here are summarized in comparison with cisplatin in Table 1.

(c) Determination of the acute toxicity

To determine the acute toxicity, NMRI mice are injected intravenously on day 0 with different doses of the test substance, dissolved in 0.5 ml of physiological saline solution. Control groups receive only 0.5 ml of physiological saline solution. 5 mice are used per concentration of the test substance. On day 14, the number of surviving mice is determined and the $LD_5$, $LD_{50}$ and $LD_{95}$ are determined therefrom by the Litchfield Wilcoxon method. The toxicity of the compounds described here is summarized in comparison with cisplatin in Table 1.

TABLE 1

| Determination of the cytostatic activity | | | |
|---|---|---|---|
| Compound | a | b | c |
| 44 | — | 0.34 | — |
| 45 | — | 0.23 | — |
| 46 | — | 0.26 | — |
| 57 | 1.9 | 0.25 | 3.4 |
| 50 | — | 0.18 | — |

EXAMPLES

The structure of the following compounds was determined by means of elemental analysis, $1_H$- and $13_C$-NMR spectroscopy and IR spectroscopy.

The course of the reactions and the resulting products were investigated by thin layer chromatography and by the HPLC technique.

The following Examples illustrate the invention in more detail, without restricting it thereto.

EXAMPLE 1

2,2-Bis-(hydroxymethyl)-1,3-diazidopropane (compound 1)

(a) 1 mole of pentaerythritol was dissolved in 600 ml of dry pyridine. 2 moles of para-toluenesulfonyl chloride were added to the stirred solution, with cooling. The reaction mixture was then stirred at room temperature for 10 hours. After the filtered solution had been concentrated in vacuo, the resulting syrup was dissolved in chloroform and the solution was extracted twice by shaking with water. The organic phase was dried and concentrated in vacuo. The product was dissolved in a mixture of 500 ml of ethanol and 400 ml of water, and 3 moles of sodium azide and 3 moles of ammonium chloride were added. After boiling under reflux for 24 hours, the reaction mixture was concentrated to a syrup in vacuo and the syrup was washed with ethyl acetate/water. The organic phase was dried and concentrated to a syrup in vacuo. The product was further purified by column chromatography (eluting agent: chloroform/acetone 4:1).

Yield: 62%.

(b) 1 mole of benzaldehyde dimethyl acetal, dissolved in 500 ml of dry dimethylformamide, and a catalytic amount of para-toluenesulfonic acid were added to 1 mole of pentaerythritol. After stirring at 60° C. for 24 hours, the cooled reaction mixture was poured into 1,000 ml of ice-water and the reaction product was taken up in diethyl ether. The organic phase was dried and concentrated in vacuo. The resulting product was dissolved in 600 ml of dry pyridine, and 2 moles of methylsulfonyl chloride, dissolved in 300 ml of dry chloroform, were added dropwise, with cooling. Thereafter, the reaction mixture was stirred at room temperature for 10 hours. The reaction mixture was concentrated to a syrup in vacuo and the syrup was washed with chloroform/water. The organic phase was dried and concentrated to a syrup in vacuo. The resulting product was dissolved in a mixture of 500 ml of ethanol and 300 ml of water, 3 moles of sodium azide and 2 moles of ammonium chloride were added and the mixture was boiled under reflux for 24 hours. The reaction mixture was concentrated to a syrup. The product was suspended in chloroform and the suspension was washed 3 times with water. The organic phase was dried and concentrated to a syrup in vacuo. The benzylidene group was split off from the reaction product in a mixture of acetic acid/sulfuric acid 100:1 at 60° C. After the reaction, the sulfuric acid was neutralized with sodium acetate and the mixture was concentrated to a syrup in vacuo. The product was further purified by column chromatography.

Yield: 73%.

IR (cm$^{-1}$): 3400, 3040-2900 and 2100.

EXAMPLE 2

2,2-bis-(methoxymethyl)-1,3-diazidopropane (compound 2)

0.5 mole of compound 1 was dissolved in 600 ml of dry dioxane. 1.2 moles of potassium tert.-butylate and 1.1 moles of methyl iodide were added at 5° C., with exclusion of moisture. After the reaction mixture had been stirred at room temperature for 15 minutes, it was concentrated in vacuo. The residue was taken up in 100 ml of ether and the mixture was washed twice with 5% strength (weight:volume) aqueous NaCl solution. The organic phase was dried with sodium sulfate and concentrated to a syrup in vacuo. The resulting product was further purified by column chromatography (eluting agent: chloroform/ethyl acetate 7:1).

Yield: 93%.

EXAMPLE 3

2,2-Bis-(octadecyloxymethyl-1,3-diazidopropane (compound 3)

0.5 mole of compound 1 was dissolved in 500 ml of dry toluene. After addition of 1.2 moles of potassium tert.-butylate and 1.05 moles of octadecyl methanesulfonate, the suspension was warmed to 70° C. and stirred under a nitrogen atmosphere for 40 minutes. After cooling, toluene was added to the reaction mixture and the salts were washed out with water. After the organic phase had been concentrated, the crude product was purified by chromatography (eluting agent: chloroform/ethyl acetate 10:1).

Yield: 82%.

The following compound was synthesized analogously: 2,2-bis-(decyloxymethyl)-1,3-diazidopropane (compound 4)

The following compounds were furthermore synthesized analogously, but 0.6 mole of potassium tert.-butylate and 0.55 mole of octadecyl or decyl methanesulfonate per 0.5 mole of compound 1 were employed in the reaction. 2-Hydroxymethyl-2-octadecyloxymethyl-1,3-diazidopropane (compound 5) and 2-decyloxymethyl-2-hydroxymethyl-1,3-diazidopropane (compound 6).

Compounds 5 and 6 were converted into methoxy derivatives as described in Example 2. 2-Methoxymethyl-2-octadecyloxymethyl-1,3-diazidopropane (compound 7) and 2-decyloxymethyl-2-methoxymethyl-1,3-diazidopropane (compound 8).

EXAMPLE 4

The following methanesulfonate or para-toluenesulfonate compounds were prepared as described in Example 1, starting from compound 1. 2-Hydroxymethyl-2-para-toluene-sulfonyloxymethyl-1,3-diazidopropane (compound 9), 2,2-bis-(para-toluenesulfonyloxymethyl)-1,3-diazidopropane (compound 10) and 2,2-bis-(methanesulfonyloxymethyl)-1,3diazidopropane (compound 11).

EXAMPLE 5

3,3-Bis-(azidomethyl)-oxetane (compound 12)

0.1 mole of compound 9 was dissolved in 100 ml of dry dioxane. 0.15 Mole of potassium tert.-butylate was added, with exclusion of moisture. After the reaction mixture had been stirred at 60° C. for 3 hours, it was concentrated. The residue was taken up in 400 ml of ether and the mixture was washed twice with 5% strength (weight: volume) aqueous NaCl solution. The organic phase was dried and concentrated in vacuo. The uniform product was further purified by column chromatography (eluting agent: chloroform/ethyl acetate 5:1).

Yield: 62%.

EXAMPLE 6

5,5-Bis-(azidomethyl)-1,3-dioxane (compound 13)

Compound 13 was prepared as in Example 1a), starting from pentaerythritol monomethylene ether.

EXAMPLE 7

5,5-Bis-(azidomethyl)-2-phenyl-1,3-dioxane (compound 14)

The preparation of compound 14 has already been described as an intermediate stage in Example 1b).

EXAMPLE 8

5,5-Bis-(azidomethyl)-2,2-bis-(methyl)-1,3-dioxane (compound 15)

1 mole of compound 1 was dissolved in 500 ml of dry acetone. After addition of 10 ml of concentrated sulfuric acid, the reaction mixture was stirred at room temperature for 2 hours. It was neutralized with calcium hydroxide and filtered and the filtrate and was concentrated to a syrup in vacuo. The crude product was further purified by column chromatography (eluting agent: chloroform/ethyl acetate 9:1).

Yield: 84%.

EXAMPLE 9

5,5-Bis-(azidomethyl)-2-methyl-2-octadecyl-1,3dioxane (compound 16)

0.8 mole of methyl octadecyl ketone was heated under reflux with 1 mole of compound 1 and 0.1 g of p-toluenesulfonic acid in 250 ml of toluene, using a water separator, until no further water of reaction was formed. After cooling, the reaction mixture was neutralized with dilute sodium hydroxide solution and concentrated to a syrup in vacuo. The product was further purified by column chromatography (eluting agent: methylene chloride/ethyl acetate 6:1).

Yield: 60%.

The following compound was prepared analogously as described in Example 9, starting from methyl octadecyl ketone and compound 1. 5,5-Bis-(azidomethyl)-2-decyl-2-methyl-1,3-dioxane (compound 17).

EXAMPLE 10

The diazido compounds 2 to 17 were converted into heir diamino derivatives in accordance with the following general working instructions.

0.1 mole of a diazido compound was dissolved in 400 ml of a mixture of methanol/ethyl acetate 2:1. After addition of 15 g of palladium-on-charcoal (10%), the reaction mixture was hydrogenated at room temperature for 3 hours, with stirring. The course of the hydrogenation was monitored by thin layer chromatography (mobile phase: chloroform/methanol/water 4:2:1 or 2:2:1). The mixture was then filtered and the filtrate was concentrated to a syrup in vacuo. The resulting product, which showed no azido band in the IR spectrum, was employed in the subsequent reaction with platinum salts without further purification steps.

Yield: 75 to 96%.

2,2-Bis-(methoxymethyl)-1,3-diaminopropane (compound 18)

2,2-Bis-(octadecyloxymethyl)-1,3-diaminopropane (compound 9)

2,2-Bis-(decyloxymethyl)-1,3-diaminopropane (compound 20)

2-Hydroxymethyl-2-octadecyloxymethyl-1,3-diaminopropane (compound 21)

2-Decyloxymethyl-2-hydroxymethyl-1,3-diaminopropane (compound 22)

2-Methoxymethyl-2-octadecyloxymethyl-1,3-diaminopropane (compound 23)

2-Decyloxymethyl-2-methoxymethyl-1,3-diaminopropane (compound 24)

2-Hydroxymethyl-2-para-toluenesulfonyloxymethyl)-1,3-diaminopropane (compound 25)

2,2-Bis-(para-toluenesulfonyloxymethyl)-1,3-diaminopropane (compound 26)

2,2-Bis-(methanesulfonyloxymethyl)-1,3-diaminopropane (compound 27)

3,3-Bis-(aminomethyl)-oxetane (compound 28)

5,5-Bis-(aminomethyl)-1,3-dioxane (compound 29)

5,5-Bis-(aminomethyl)-2-phenyl-1,3-dioxane (compound 30)

5,5-Bis-(aminomethyl)-2,2-bis-(methyl)-1,3-dioxane (compound 31)

5,5-Bis-(aminomethyl)-2-methyl-2-octadecyl-1,3-dioxane (compound 32) and
5,5-Bis-(aminomethyl)-2-decyl-2-methyl-1,3-dioxane (compound 33).

EXAMPLE 11

The diamino compounds 18 to 33 were converted into platinum complexes in accordance with the following general working instructions.

60 mmol of diamino compound were dissolved in 50 ml of distilled, degased water. The solution was added dropwise to 60 mmol of potassium tetrachloroplatinate, dissolved in 60 ml of water, in the course of 2 hours, with stirring. The reaction mixture was stirred at room temperature for a further 20 hours, with exclusion of light, the platinum complex being obtained as a precipitate in the course of the reaction. The thin layer chromatogram of the reaction (mobile phase: chloroform/methanol/water 4:4:1; spray reagents: ninhydrin and tin dichloride) showed that the ninhydrin-active starting compound had reacted completely. The precipitate was filtered off at 0° C., washed with cold water and, if necessary, recrystallized from dimethylformamide and water. The filtrate was concentrated to a volume of about 15 ml in vacuo and the concentrate was cooled to 0° C. The compound precipitated was worked up in the same manner as the main fraction. The product was dried under a high vacuum for a further 3 days.

Yield: 80% to 92%.

2,2-Bis-(methoxymethyl)-1,3-diaminopropane-platinum(II) dichloride (compound 34)
2,2-Bis-(octadecyloxymethyl)-1,3-diaminopropane-platinum(II) dichloride (compound 35)
2,2-Bis-(decyloxymethyl)-1,3-diaminopropane-platinum(II) dichloride (compound 36)
2-Hydroxymethyl-2-octadecyloxymethyl-1,3-diaminopropaneplatinum(II) dichloride (compound 37)
2-Decyloxymethyl-2-hydroxymethyl-1,3-diaminopropane-platinum(II) dichloride (compound 38)
2-Methoxymethyl-2-octadecyloxymethyl-1,3-diaminopropane-platinum(II) dichloride (compound 39)
2-Decyloxymethyl-2-methoxymethyl-1,3-diaminopropane-platinum(II) dichloride (compound 40)
2-Hydroxymethyl-2-para-toluenesulfonyloxymethyl)-1,3-di- aminopropane-platinum(II) dichloride (compound 41)
2,2-Bis-(para-toluenesulfonyloxymethyl)-1,3-diaminopropane-platinum(II) dichloride (compound 43)
2,2-Bis-(methanesulfonyloxymethyl)-1,3-diaminopropane-platinum(II) dichloride (compound 43)
3,3-Bis-(aminomethyl)-oxetane-platinum(II) dichloride (compound 44)
5,5-Bis-(aminomethyl)-1,3-dioxane-platinum(II) dichloride (compound 45)
5,5-Bis-(aminomethyl)-2-phenyl-1,3-dioxane-platinum(II) dichloride (compound 46)
5,5-Bis-(aminomethyl)-2,2-bis-(methyl)-1,3-dioxane-platinum(II) dichloride (compound 47)
5,5-Bis-(aminomethyl)-2-methyl-2-octadecyl-1,3-dioxane-platinum(II) dichloride (compound 48) and
5,5-Bis-(aminomethyl)-2-decyl-2-methyl-1,3-dioxane-platinum(II) dichloride (compound 49)

EXAMPLE 12

α,α',α", α'''-Tetraamineneopentane-platinum(II) dichloride (compound 50)

0.1 mole of α,α', α", α'''-tetraamineneopentane was reacted with 0.2 mole of potassium tetrachloroplatinate as described in Example 11 to give compound 50.

EXAMPLE 13

5,5-Bis-(aminomethyl)-1,3-dioxane-platinum(II) diiodide (compound 51)

2.44 mmol of potassium tetrachloroplatinate and 2.44 mmol of potassium iodide were suspended in 15 ml of water. After 30 minutes, 2.44 mmol of compound 29, dissolved in 5 ml of water, were added dropwise to the resulting solution in the course of 1 hour, with stirring. The reaction mixture was stirred at room temperature for 20 hours, with exclusion of light, during which compound 51 was obtained as a precipitate. The precipitate was filtered off at 0° C., washed with water and ethanol and recrystallized from water and dimethylformamide. The product was dried in a high vacuum for a further 3 days.

Yield: 83%.

EXAMPLE 14

2,2-Bis-(methoxymethyl)-1,3-diaminopropane-platinum(II) hydroxide (compound 52)

(a) 24 mmol of compound 34 were suspended in 500 ml of distilled, degased water. After addition of 48 mmol of silver nitrate, dissolved in 200 ml of water, the reaction mixture was stirred at room temperature for 40 hours, with exclusion of light. The silver chloride precipitated was then filtered off and the filtrate was concentrated to a volume of 350 ml in vacuo. The resulting intermediate - 2,2-bis-(hydroxymethyl)-1,3-diamino-propane-platinum(II) - was used in the following reaction without further purification steps.

(b) 25 g of ion exchange resin (Dowex, type 1×8; activation with 10 N NaOH) were added to the solution with the dinitrate intermediate, with stirring. After 30 minutes, the thin layer chromatogram (n-butanol/glacial acetic acid/water 5:3:2; cellulose foil) showed that replacement of the nitrate by hydroxyl had gone to completion. After the resin had been filtered off, the filtrate was concentrated to dryness in vacuo, with exclusion of light.

Yield: 85%.

The following compounds were prepared analogously:

2,2-Bis-(octadecyloxymethyl)-1,3-diamino-platinum(II) hydroxide (compound 53)
3,3-Bis-(aminomethyl)-oxetane-platinum(II) hydroxide (compound 54)
5,5-Bis-(aminomethyl)-1,3-dioxane-platinum(II) hydroxide (compound 55)
5,5-Bis-(aminomethyl)-2,2-bis-(methyl)-1,3-dioxane-platinum(II) hydroxide (compound 56)
5,5-Bis-(aminomethyl)-2-methyl-2-octadecyl-1,3-dioxane-platinum(II) hydroxide (compound 57)
α, α', α", α'''-Tetraaminoneopentane-platinum(II) hydroxide (compound 58).

EXAMPLE 15

Di- and oligo-carboxylic acid derivatives were prepared by the following process, starting from platinum-(II) hydroxide compounds 52 to 58.

13 mmol of a platinum(II) hydroxide compound were dissolved in 50 ml of distilled, degased water. 13 mmol of a di- or oligo-carboxylic acid were added to this solution, while stirring and with exclusion of light. After 6 hours, the reaction solution was evaporated to dryness in vacuo and then concentrated in a high vacuum.

Yield: 100%.

5,5-Bis-(aminomethyl)-2,2-bis-(methyl)-1,3-dioxane-platinum(II) anion

| Anion | Compound No. |
|---|---|
| Malonate | 59 |
| Maleate | 60 |
| 1,1-Cyclobutane-dicarboxylate | 61 |
| 1,2-Cyclobutane-dicarboxylate | 62 |
| 3-Carboxylphthalate | 63 |
| 4-Carboxylphthalate | 64 |
| 3,6,9-Trioxanona-2,9-dicarboxylate | 65 |
| Polyglutamic acid anion | 66 |
| Chondroitin sulfate | 67 |

2,2-Bis-(methoxymethyl)-1,3-diaminopropane-platinum(II) anion

| Anion | Compound No. |
|---|---|
| Malonate | 68 |
| 1,1-Cyclobutane-dicarboxylate | 69 |
| Polyglutamic acid anion | 70 |

2,2-Bis-(octadecyloxymethyl)-1,3-diamino-platinum(II) anion

| Anion | Compound No. |
|---|---|
| Malonate | 71 |
| 1,1-Cyclobutane-dicarboxylate | 72 |

3,3-Bis-(aminomethyl)-oxetane-platinum(II) anion

| Anion | Compound No. |
|---|---|
| Malonate | 73 |
| 1,1-Cyclobutane-dicarboxylate | 74 |
| Polyglutamic acid anion | 75 |

5,5-bis-(aminomethyl)-1,3-dioxane-platinum(II) anion

| Anion | Compound No. |
|---|---|
| Malonate | 76 |
| Maleate | 77 |
| 1,1-Cyclobutane-dicarboxylate | 78 |
| 3-Carboxylphthalate | 79 |
| Polyglutamic acid anion | 80 |

5,5-Bis-(amiomethyl)-2-methyl-2-octadecyl-1,3-dioxane-platinum(II) anion

| Anion | Compound No. |
|---|---|
| Malonate | 81 |
| 1,1-Cyclobutane-dicarboxylate | 82 |

$\alpha, \alpha', \alpha'', \alpha'''$-Tetraaminoneopentane-platinum(II) anion

| Anion | Compound No. |
|---|---|
| Malonate | 83 |
| 1,1-Cyclobutane-dicarboxylate | 84 |
| Polyglutamic acid anion | 85 |

EXAMPLE 16

5,5-Bis-(aminomethyl)-1,3-dioxane-platinum(II) diacetate (compound 86)

12 mmol of compound 47 was suspended in 300 ml of distilled, degased water. After addition of 24 mmol of silver acetate, the reaction batch was stirred intensively at room temperature for 40 hours, with exclusion of light. The silver chloride precipitated was then filtered off and the filtrate was concentrated to the dry product in vacuo. The product was dried in a high vacuum for a further 3 hours.

The following compounds were prepared analogously, starting from compound 47, which was reacted with silver(I) trifluoroacetate, trifluorosulfonate, p-toluenesulfonate or perchlorate:

5,5-Bis-(aminomethyl)-1,3-dioxane-platinum(II) dianion

| Anion | Compound No. |
|---|---|
| trifluoroacetate | 87 |
| trifluoromethanesulfonate | 88 |
| p-toluenesulfonate | 89 |
| perchlorate | 90 |

EXAMPLE 17

Compounds 91 and 92 were prepared as described in Example 3 starting from compound 1 and $CH_c$—$(OCH_2CH_2)_c$—O—$SO_2CH_3$, where c=3 or 6. Compounds 91 and 92 were converted into the corresponding amino compounds, which were complexed with potassium tetrachloroplatinate, as described in Examples 10 and 11, compounds 93 and 94 being formed.

| | Compound No. | c |
|---|---|---|
| $CH_3$—$(O—CH_2—CH_2)_c$—O—$CH_2$\\C/$CH_2$—$N_3$ / $CH_3$—$(O—CH_2—CH_2)_c$—O—$CH_2$/ \\$CH_2$—$N_3$ | 91 | 3 |
| | 92 | 6 |

-continued
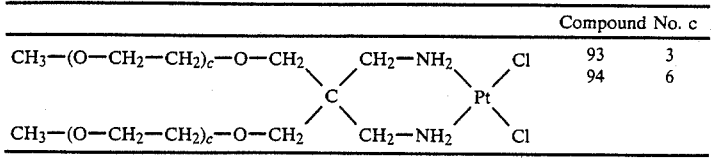
| | Compound No. | c |
|---|---|---|
| | 93 | 3 |
| | 94 | 6 |
TABLE 2
Elemental analysis
| Compound No. | C % | H % | Cl % | N % | Pt % | C % | H % | Cl % | N % | Pt % |
|---|---|---|---|---|---|---|---|---|---|---|
| 34 | 19.63 | 4.24 | 16.56 | 6.54 | 45.56 | 19.51 | 4.19 | 16.12 | 6.51 | 45.13 |
| 35 | 54.41 | 9.58 | 7.83 | 3.09 | 21.55 | 54.14 | 9.49 | 7.84 | 3.01 | 21.64 |
| 36 | 54.41 | 8.00 | 10.42 | 4.12 | 28.66 | 54.40 | 7.96 | 10.31 | 4.03 | 28.34 |
| 37 | 42.33 | 7.72 | 10.86 | 4.29 | 29.89 | 42.18 | 7.64 | 10.69 | 4.16 | 29.17 |
| 38 | 33.34 | 6.34 | 13.12 | 5.18 | 36.10 | 33.16 | 6.33 | 12.96 | 5.16 | 35.97 |
| 39 | 43.24 | 7.86 | 10.64 | 4.20 | 29.26 | 43.19 | 7.71 | 10.53 | 4.09 | 29.21 |
| 40 | 34.66 | 6.54 | 12.79 | 5.05 | 35.18 | 34.72 | 6.56 | 12.72 | 5.00 | 34.89 |
| 41 | 26.00 | 3.64 | 12.79 | 5.05 | 35.19 | 26.11 | 3.67 | 12.71 | 5.05 | 35.17 |
| 42 | 32.21 | 3.70 | 10.01 | 3.95 | 27.53 | 32.12 | 3.71 | 10.12 | 3.98 | 27.83 |
| 43 | 15.11 | 3.26 | 12.74 | 5.04 | 35.07 | 15.02 | 3.17 | 12.84 | 4.87 | 35.14 |
| 44 | 15.71 | 3.17 | 18.55 | 7.33 | 51.05 | 15.72 | 3.16 | 18.57 | 7.24 | 51.21 |
| 45 | 17.48 | 3.42 | 17.20 | 6.80 | 47.33 | 17.43 | 3.40 | 17.24 | 6.51 | 46.94 |
| 46 | 30.52 | 3.84 | 15.01 | 5.93 | 41.31 | 30.36 | 3.80 | 15.07 | 5.76 | 41.00 |
| 47 | 21.83 | 4.12 | 16.11 | 6.36 | 44.31 | 21.80 | 4.11 | 16.32 | 6.32 | 44.07 |
| 48 | 46.43 | 8.11 | 10.96 | 4.33 | 30.17 | 46.21 | 8.07 | 10.97 | 4.19 | 30.12 |
| 49 | 36.04 | 6.41 | 12.52 | 4.95 | 34.44 | 36.01 | 6.44 | 12.42 | 4.93 | 34.14 |
| 50 | 9.04 | 2.43 | 21.35 | 8.44 | 58.74 | 9.00 | 2.41 | 21.37 | 8.41 | 58.81 |
| 51 | 12.11 | 2.37 | — | 4.71 | 32.78 | 12.03 | 2.32 | — | 4.63 | 32.16 |
| 52 | 21.41 | 5.15 | — | 7.16 | 49.85 | 21.34 | 5.13 | — | 7.11 | 49.53 |
| 53 | 56.72 | 10.22 | — | 3.23 | 22.47 | 56.72 | 10.19 | — | 3.12 | 22.31 |
| 54 | 17.39 | 4.09 | — | 8.11 | 56.50 | 17.26 | 4.06 | — | 8.02 | 56.41 |
| 55 | 19.20 | 4.30 | — | 7.46 | 51.98 | 19.21 | 4.32 | — | 7.36 | 51.34 |
| 56 | 23.82 | 5.00 | — | 6.95 | 48.37 | 23.73 | 4.93 | — | 6.82 | 48.07 |
| 57 | 46.79 | 8.48 | — | 4.36 | 30.40 | 46.63 | 8.48 | — | 4.32 | 30.29 |
| 58 | 10.17 | 3.41 | — | 9.49 | 66.09 | 10.11 | 3.40 | — | 9.52 | 66.12 |
| 59 | 28.03 | 4.28 | — | 5.94 | 41.39 | 28.01 | 4.27 | — | 5.91 | 41.07 |
| 60 | 29.82 | 4.17 | — | 5.80 | 40.36 | 29.56 | 4.09 | — | 5.78 | 40.19 |
| 61 | 32.88 | 4.73 | — | 5.48 | 38.14 | 32.86 | 4.73 | — | 5.37 | 38.16 |
| 62 | 32.88 | 4.73 | — | 5.48 | 38.14 | 32.88 | 4.71 | — | 5.41 | 38.07 |
| 63 | 35.36 | 3.84 | — | 4.85 | 33.78 | 35.32 | 3.79 | — | 4.80 | 33.69 |
| 64 | 35.36 | 3.84 | — | 4.85 | 33.78 | 35.29 | 3.83 | — | 4.81 | 33.21 |
| 65 | 32.60 | 5.13 | — | 4.75 | 33.09 | 32.60 | 5.12 | — | 4.76 | 33.10 |
| 66 | — | — | — | — | 31.1 | — | — | — | — | 30.27 |
| 67 | — | — | — | — | 14.94 | — | — | — | — | 14.03 |
| 68 | 24.64 | 4.14 | — | 5.75 | 40.03 | 24.61 | 4.16 | — | 5.71 | 39.73 |
| 69 | 31.26 | 4.84 | — | 5.61 | 39.06 | 31.12 | 4.78 | — | 5.49 | 39.01 |
| 70 | — | — | — | — | 31.71 | — | — | — | — | 31.11 |
| 71 | 56.44 | 9.47 | — | 2.99 | 20.84 | 56.42 | 9.46 | — | 2.93 | 20.76 |
| 72 | 57.82 | 9.50 | — | 2.87 | 19.98 | 57.80 | 9.47 | — | 2.90 | 19.43 |
| 73 | 23.25 | 3.41 | — | 6.78 | 47.20 | 23.21 | 3.40 | — | 6.72 | 47.02 |
| 74 | 29.14 | 4.00 | — | 6.18 | 43.03 | 29.07 | 3.99 | — | 6.16 | 43.01 |
| 75 | — | — | — | — | 34.28 | — | — | — | — | 33.85 |
| 76 | 24.38 | 3.64 | — | 6.32 | 44.01 | 24.32 | 3.63 | — | 6.27 | 44.07 |
| 77 | 26.38 | 3.54 | — | 6.15 | 42.15 | 26.38 | 3.54 | — | 6.17 | 42.18 |
| 78 | 29.12 | 4.17 | — | 5.80 | 40.36 | 29.13 | 4.15 | — | 5.81 | 40.43 |
| 79 | 32.79 | 3.30 | — | 5.10 | 35.51 | 32.69 | 3.27 | — | 5.03 | 35.36 |
| 80 | — | — | — | — | — | — | — | — | — | — |
| 81 | 47.38 | 7.67 | — | 3.95 | 27.48 | 47.29 | 7.64 | — | 3.82 | 27.17 |
| 82 | 49.65 | 7.80 | — | 3.74 | 26.02 | 49.65 | 7.67 | — | 3.72 | 26.07 |
| 83 | 18.19 | 2.78 | — | 7.71 | 53.71 | 18.19 | 2.69 | — | 7.73 | 53.82 |
| 84 | 25.31 | 3.50 | — | 6.95 | 48.37 | 25.31 | 3.49 | — | 6.94 | 48.12 |
| 85 | — | — | — | — | 37.61 | — | — | — | — | 27.23 |
| 86 | 26.15 | 4.39 | — | 6.10 | 42.47 | 26.15 | 4.38 | — | 6.07 | 42.43 |
| 87 | 17.69 | 2.60 | — | 5.16 | 35.91 | 17.53 | 2.57 | — | 5.11 | 35.90 |
| 88 | 15.03 | 2.21 | — | 4.38 | 30.51 | 15.00 | 2.20 | — | 4.32 | 30.38 |
| 89 | 35.14 | 4.13 | — | 4.10 | 28.54 | 35.17 | 4.11 | — | 4.08 | 28.13 |
| 90 | 13.34 | 2.61 | 13.13 | 5.19 | 36.12 | 13.33 | 2.59 | 13.17 | 5.08 | 36.02 |
We claim:
1. A compound of the formula I or II
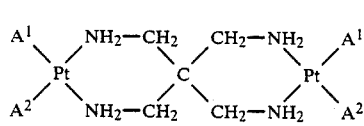
Formula I
-continued
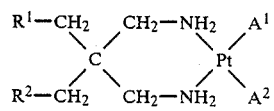
Formula II in which $R^1$ and $R^2$ independently of one another represent $H-(CH_2)_a-(O-CH_2)_b)_c-O$, where $a=0$ to 4, $b=1$ to 4 and $c=1$ to 7, an alkoxy or arylalkoxy group with 1 to 20 carbon atoms, an alkane- or aralkanesulfonyloxy group with 1 to 7 carbon atoms or a tetrahydropyranyloxy radical, or $R^1$ and $R^2$ together represent an oxygen atom bonded in an ether-like manner or an acetal or ketal radical

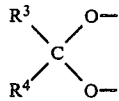

where $R^3$ and $R^4$ independently or one another represent a hydrogen atom, an alkyl group with 1 to 20 carbon atoms or a phenyl group, $A^1$ and $A^2$ are identical and represent a hydroxyl group, chloride, bromide, iodide, nitrate, acetate, trifluoroacetate, trifluorosulfonate or perchlorate, or $A^1$ represents sulfate or carbonate and $A^2$ represents $H_2O$, or $A^1$ or $A^2$ together represent the diamion or an organic acid selected from the group consisting of oxalic, malonic, hydroxymalonic, ethylmalonic, succinic, maleic, aconitic, 3,6,9-trioxaundecanedioic, 1- or 1,2-cyclobutanedicarboxylic, phthalic, 3- or 4- carboxyphthalic and 3,4-dicarboxyphthalic acid, or $A^1$ and $A^2$ together represent a recurring anionic unit of a polymeric compound selected from the group consisting of dextran sulfate, chondroitin sulfate, galactan sulfate, polyglutamic acid or polyitaconic acid.

* * * * *

UNITED STATES PATENT AND TRADEMARK OFFICE
CERTIFICATE OF CORRECTION

PATENT NO. : 4,730,069

DATED : March 8, 1988

INVENTOR(S) : Cenek Kolar et al.

It is certified that error appears in the above-identified patent and that said Letters Patent is hereby corrected as shown below:

Claim 1, Line 9, Column 16, change "1" to --1,1- --.

Claim 1, Line 6, Column 16, change "diamion" to --dianion--.

Signed and Sealed this

Twenty-eighth Day of February, 1989

*Attest:*

DONALD J. QUIGG

*Attesting Officer*      *Commissioner of Patents and Trademarks*

UNITED STATES PATENT AND TRADEMARK OFFICE
CERTIFICATE OF CORRECTION

PATENT NO. : 4,730,069

DATED : March 8, 1988

INVENTOR(S) : Cenek Kolar, Hans P. Kraemer, Konrad Dehmel

It is certified that error appears in the above-identified patent and that said Letters Patent is hereby corrected as shown below:

Column 15, line 2, change "$H-(CH_2)_a-(O-CH_2)_b)_c-O$" to --$H-(CH_2)_a-(O-(CH_2)_b)_c-O$--;

Column 15, line 15, change "or" to --of--;

Column 16, line 6, change "or" to --of--.

Signed and Sealed this

Twenty-fifth Day of February, 1992

*Attest:*

HARRY F. MANBECK, JR.

*Attesting Officer*      *Commissioner of Patents and Trademarks*